United States Patent [19]
Yuan et al.

[11] Patent Number: 5,676,701
[45] Date of Patent: Oct. 14, 1997

[54] LOW WEAR ARTIFICIAL SPINAL DISC

[75] Inventors: Hansen A. Yuan, Fayetteville, N.Y.; Chih-I Lin, Diamond Bar, Calif.; James A. Davidson, Germantown, Tenn.; Laura C. Small, Memphis, Tenn.; Thomas A. Carls, Memphis, Tenn.

[73] Assignee: Smith & Nephew, Inc., Memphis, Tenn.

[21] Appl. No.: 480,762

[22] Filed: Jun. 7, 1995

Related U.S. Application Data

[63] Continuation-in-part of Ser. No. 4,607, Jan. 14, 1993, abandoned.

[51] Int. Cl.$^6$ .................................................. A61F 2/44
[52] U.S. Cl. .................................................. 623/17; 606/61
[58] Field of Search .................... 623/16, 17; 606/60, 606/61

[56] References Cited

U.S. PATENT DOCUMENTS

| | | |
|---|---|---|
| 4,349,921 | 9/1982 | Kuntz . |
| 4,759,766 | 7/1988 | Buettner-Janz et al. . |
| 4,997,432 | 3/1991 | Keller . |
| 5,258,031 | 11/1993 | Salib et al. . |
| 5,258,043 | 11/1993 | Stone . |
| 5,306,307 | 4/1994 | Senter et al. . |
| 5,306,308 | 4/1994 | Gross et al. . |
| 5,306,309 | 4/1994 | Wagner et al. . |
| 5,308,412 | 5/1994 | Shetty et al. . |
| 5,314,477 | 5/1994 | Marnay ........................ 623/17 |
| 5,401,269 | 3/1995 | Büttner-Janz et al. . |
| 5,415,704 | 5/1995 | Davidson ..................... 623/16 |
| 5,425,773 | 6/1995 | Boyd et al. . |

FOREIGN PATENT DOCUMENTS

| | | |
|---|---|---|
| 0042271 | 12/1981 | European Pat. Off. . |
| 0 176 728 | 4/1986 | European Pat. Off. . |
| 0 699 426 A1 | 3/1996 | European Pat. Off. . |
| 2632516 | 12/1989 | France . |
| 2694882 | 2/1994 | France . |
| 2 718 635 | 10/1995 | France . |
| 2263842 | 7/1974 | Germany . |
| 3023-353 | 4/1981 | Germany . |
| WO 91/13598 | 9/1991 | WIPO . |
| WO 93/10725 | 6/1993 | WIPO . |

*Primary Examiner*—Debra S. Brittingham
*Attorney, Agent, or Firm*—Pravel, Hewitt, Kimball & Krieger

[57] ABSTRACT

An artificial spinal disc for surgical placement between adjacent vertebrae including a first component for attaching to a first vertebrae, the first component having a concave recess, with the concave contoured surface having a circumference of 360°. A second component for attaching to a second vertebrae, the second component including a projection with a convex surface, the convex contoured surface having a circumference of 360°. The corresponding contoured surfaces shaped to allow an unrestricted rotational and a flexion/extension bending motion between the first and second components relative to a patient's normal spinal axis when in a standing position with the spine in a straightened position.

10 Claims, 3 Drawing Sheets

LOW WEAR ARTIFICIAL SPINAL DISC

This is a continuation-in-part application of application U.S. Ser. No. 08/004,607, filed Jan. 14, 1993, now abandoned and fully incorporated herein by reference.

FIELD OF THE INVENTION

The present invention relates to an artificial intervertebral disc, and more particularly to a low wear, hard chromium-containing metal ball and socket bearing system allowing unrestricted motion for use in the replacement of spinal disc segments.

BACKGROUND OF THE INVENTION

There have been numerous types of implants designed to replace damaged spinal disc segments of the human body in which an artificial intervertebral disc is used to replace a deformed, injured or diseased natural intervertebral disc. Such an artificial intervertebral disc is generally composed of a rigid solid body that causes the vertebrae adjacent to the implanted artificial disc to be limited in its ability to move relative to each other. Some of these solid body artificial intervertebral discs are disclosed in U.S. Pat. Nos. 4,349,921; 4,553,273; and 4,714,469. Other artificial discs are provided with a spring which permits the vertebrae adjacent to the implanted artificial disc to have a limited mount of motion in limited directions. These are described in U.S. Pat. Nos. 4,309,777 and 4,759,769.

It has also been proposed that soft compliant polymers be used to assure separation of damaged disc segments or as bearing surfaces. However, polymers can degrade with time in the human body and also be susceptible to abrasion damage by the bone surface. Further, polymeric disc replacements are susceptible to creep and gradual changes in dimensional characteristics. But polymers are favored due to their low stiffness and relative improvement in shock absorbing characteristics. Artificial intervertebral discs having a main body formed of an elastic polymer are disclosed in U.S. Pat. Nos. 3,867,729; 4,863,477 and 4,911,71. U.S. Pat. No. 5,071,437 discloses an artificial intervertebral disc composed of an elastomeric core sandwiched between two metal plates. This disc is further provided with a plurality of spikes for stabilizing the vertebrae adjacent to the implanted disc. However, the biocompatability of this disc is uncertain because it contains a polymer and a curing agent used to hold the metal plates and the elastomeric core together.

Ball and socket type artificial spinal discs have been proposed but, without polymer components they have less shock absorbing capabilities. Further, there is no clinical proof that shock absorption is necessary, as adjacent discs can compensate for a reduced level of shock absorption in one or two discs along the entire spinal column.

Non-polymeric disc components include ceramic and metal materials and designs have included hinged, sliding and ball and socket-type solutions. The hinged design frequently is constraining, and the patient cannot effectively move in some directions. Sliding disc surfaces generally do not have the ability to accommodate bending or twisting motion, but do help assist with natural translation motion tendencies within the disc space. However, due to the small space between adjacent vertebrae, the contact stress with only this type of single (translation) motion capability between the sliding surfaces can lead to excessive wear and eventual disfunction of the artificial intervertebral disc.

The most logical solution for spinal disc replacement is the ball and socket-type design. Ceramics have been proposed, but ceramic surfaces are extremely hard and prone to excessive contact stress and wear if three-body particles or debris become lodged between the two surfaces. Without film lubrication to separate the two ceramic surfaces, high hertzian contact stresses can fracture the hard surface, leading to continued and accelerated surface wear damage. Debris, such as bone chips, can readily create this adverse three-body wear process. Further, because of the relatively high stiffness of ceramics, implant design and machining must be such that surface contact is optimized. Such precision machining is extremely difficult to accomplish with ceramic surfaces.

Hard, metal surfaces which are passivated by relatively soft, lubricious oxides and oxyhydroxides (i.e., Cr-containing metals) are much more tolerant to the occasional severe, high contact stress wear conditions found in the vertebral column. However, this type of ball and socket system is only effective under normal, non-extreme motion. During extreme motion and bending of the spinal column, the ball can "rock out" of the socket and impinge the device edges, creating high stresses and wear. Metals would be more tolerant under these extreme conditions than hard ceramic, but metal components can also experience some wear conditions. Therefore, allowance in the implant design to minimize contact stress in these extreme motion conditions is also desirable.

Other designs using either ceramic or metal materials also restrict motion relative to the adjacent vertebrae. Some skilled in the art feel that, because the natural healthy disc experiences a limit of about 11° motion in the anterior-posterior plane (bending forward/backward) and a limit of about 3°–5° motion in the medial-lateral plane (bending side-to-side), the artificial disc replacement must also have this limitation, which causes other adjacent discs to take up the strain, Further, some skilled in the art argue that there must be a restriction to rotation (1°–2°) within the artificial disc for the same reasons. For example, U.S. Pat. No. 4,759,769 discloses a hinged/spring design with a limitation of 20° in flexion/extension and allowance of a small amount of side-to-side rocking. Rotation is restricted with this device. U.S. Pat. No. 5,071,437 describes an implant device that limits flexion/extension and lateral bending to physiologic angles and allows for only 2°–3° of rotation. This device also allows for 1–2 mm of transition. U.S. Pat. No. 4,759,766 describes a device composed of two cobalt/chrome end plates with a domed polyethylene central core which allows 10° flexion/extension, a small amount of lateral bending, and is rotationally restricted. The addition of these anatomical restrictions to disc replacement designs limit the type and effectiveness of the design and the materials that may be employed. For example, if the disc prosthesis exceeds its 11° bending restriction, than as mentioned above, the non-bearing surfaces will contact each other and inappropriately displace the prosthesis or create an adverse wear situation.

It is felt that restrictions in disc prosthesis design may not only create a performance liability, but are also not needed. The surrounding ligaments, muscles, and other tissues provide a built-in restriction to anterior/posterior, medial-lateral, and twisting motions of the artificial intervertebral disc, at least to a point in which adjacent discs are not significantly affected.

For the reasons mentioned above, the present invention provides an unrestricted ball and socket-type artificial spinal disc containing low wear bearing surfaces of chromium containing metals, precision machined to minimize contact stress and anchored to the adjacent vertebrae with press fit or cemented methods known in the art of joint replacement. To accommodate extreme motion, the peripheral areas of the ball and socket type intervertebral disc are designed to minimize stress and wear. This design can also incorporate the ability to translate, similar to that for a miniscal bearing knee. Additionally, the bearing portions of the disc of the artificial intervertebral disc can be attached to a different material for anchoring the disc portions to the adjacent bone.

SUMMARY OF THE INVENTION

The present invention provides an artificial spinal disc for surgical placement between adjacent vertebrae. The apparatus of the present invention provides a low wear artificial spinal disc that includes a first component for attaching to a first vertebrae having a concave recess, with the concave contoured surface having a circumference of 360°. A second component for attaching to a second vertebrae has a projection that fits the concave recess of the first component, with the convex contoured surface having a circumference of 360°. The corresponding contoured surfaces allow an unrestricted rotational and a relatively unrestricted flexion/extension bending motion between the first and second components relative to a patient's normal spinal axis when in a standing position with the spine in a straightened position.

BRIEF DESCRIPTION OF THE DRAWINGS

The invention will become more apparent when the detailed description of exemplary embodiments is considered in conjunction with the appended drawings, in which.

DETAILED DESCRIPTION OF PREFERRED EMBODIMENTS

Figure 10:
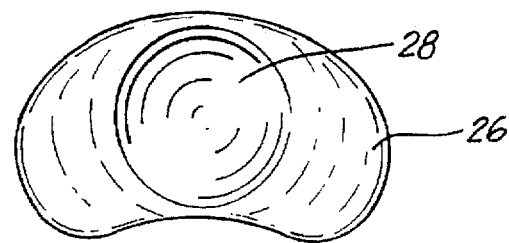
FIG. 10 is a plan view of the inner side of the first component as shown in FIG. 5.

As shown in FIGS. 1–4, a low wear artificial spinal or intervertebral disc 10 of the present invention includes a first component or intervertebral support block 20 for attaching to the end plate of a first vertebrae and a second component or intervertebral bearing block 30 for attaching to the end plate of a second adjoining vertebrae. The intervertebral support block 20 has an outer side 22 provided with one or more protuberances 24 such as pegs, posts or screws and an inner side 26 which has a concave recess or recessed receiving mount 28 forming a socket-like segment located near the center of the support block 20 (FIG. 10). The concave contoured surface of the receiving mount 28 has a circumference of 360°.

Figure 1:
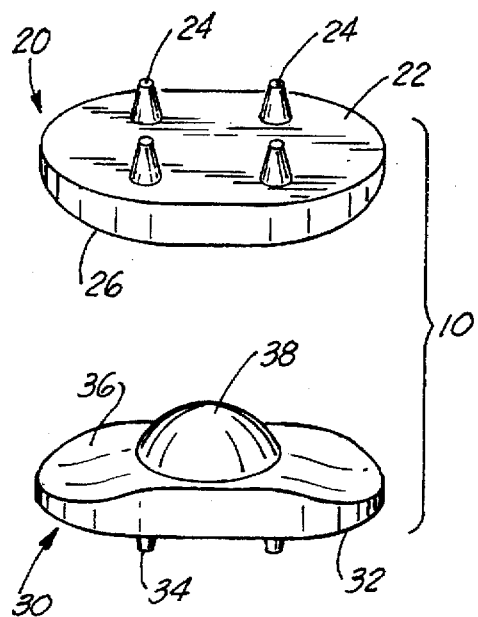
FIG. 1 is an exploded view of the present invention.
Figure 2:
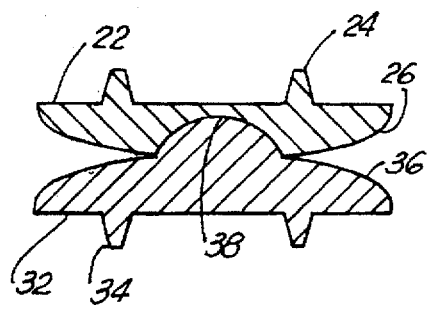
FIG. 2 is a side sectional view of the present invention as shown in FIG. 1.
Figure 3:
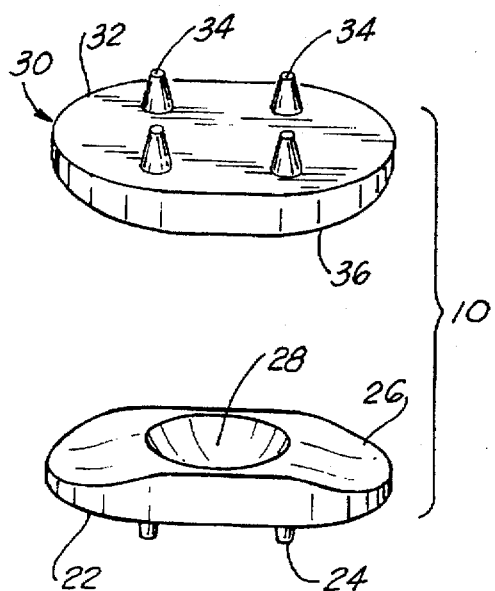
FIG. 3 is the reverse of the exploded view of the present invention as shown in FIG. 1.
Figure 4:
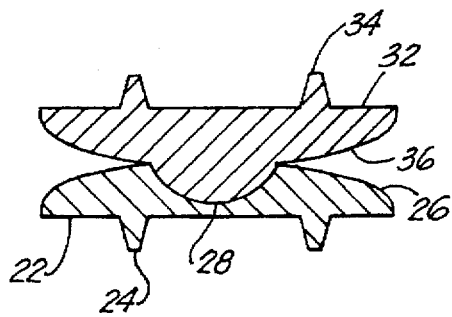
FIG. 4 is a side sectional view of the present invention as shown in FIG. 3.
Figure 5:
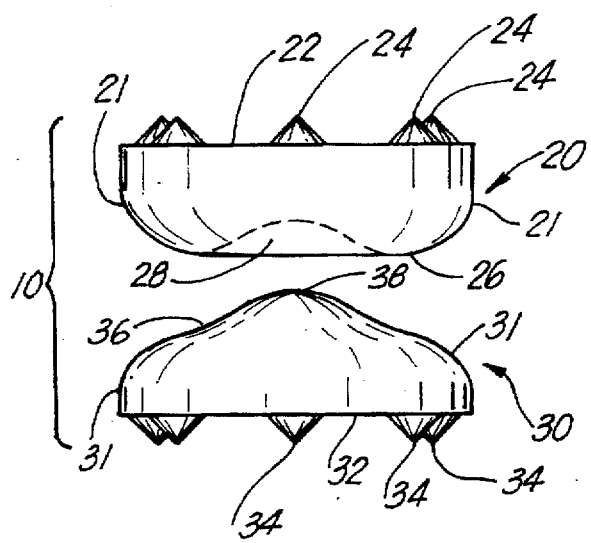
FIG. 5 is a side elevational view of an alternate shape of the present invention.
Figure 11:
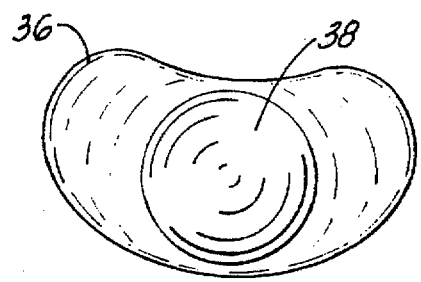
FIG. 11 is a plan view of the inner side of the second component as shown in FIG. 5.
Figure 12:
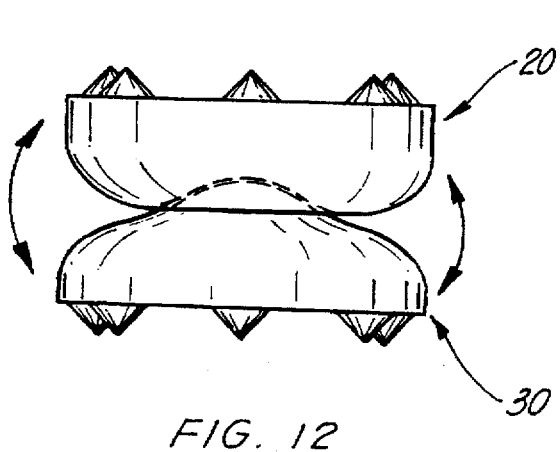
FIG. 12 is a side, partial phantom, view of the components of the present invention in a joined relation.
Figure 13:
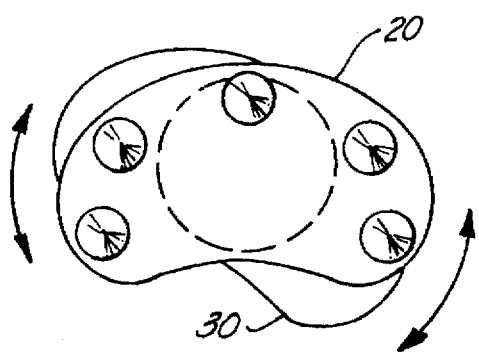
FIG. 13 is a top plan view of the components of the present invention in a joined relation showing rotational motion.

The intervertebral bearing block 30 has an outer side 32 with one or more protuberances 34, such as pegs, posts or screws, and an inner side 36 which has a projection 38 with a convex surface forming a ball-like segment (FIG. 11), the convex surface having a circumference of 360°. The projection 38 corresponds in location to the recessed receiving mount 28 of the supporting block 20 and is shaped so as to fit rotatably into the recessed receiving mount 28 of the supporting block 20, as shown in FIGS. 10–12. The projection 38 of the bearing block 30 and the recessed receiving mount 28 of the supporting block 20 are shaped so as to form a ball and socket-type device which allows for unrestricted rotational (FIG. 13) and relatively unrestriced flexion/extension bending motion (FIG. 12) between the supporting block 20 and bearing block 30 relative to a patient's normal spinal axis when in a standing position with the spine in a straightened position. The inner side 26 of the supporting block 20 and the inner side 36 of the bearing block 30 are provided respectively with a surface curving or sloping slightly outwards to a periphery 21, 31 respectively of the supporting block 20 and bearing block 30, as shown in FIGS. 2–4, 5 and 7. Thus, the inner side 26 of the supporting block 20 has inclined surfaces between the periphery 21 of the supporting block 20 and the recessed receiving mount 28. Likewise, the inner side 36 of the bearing block 30 has inclinded surfaces between the periphery 31 of the bearing block 30 and the projection 38, as shown in FIGS. 5 and 12.

As a result, the configuration of the supporting block 20 and bearing block 30 allows for a considerable angle of flexion/extension generally of about between 20°–30° within which each can turn, as illustrated in FIG. 12, thereby enabling a patient with the implanted artificial intervertebral disc 10 to have generally normal motion and rotation of the spinal column.

The outer sides 22 and 32 of the intervertebral supporting block 20 and intervertebral bearing block 30 can be substantially flat, slightly concave, or curved in various forms. However, flat or slightly concave outer surfaces are preferable and can be covered with a coating of material corresponding to the material that forms the supporting block 20 and the bearing block 30. Such coated outer surfaces are similar in formation to those disclosed in U.S. Pat. No. 5,071,437.

With the exception of the recessed receiving mount 28, the inner side 26 of the supporting block 20 is substantially flat or slightly convex. A slightly convex inner side 26 is preferable because such a surface enables the supporting block 20 and the bearing block 30 to rotate 360° relative to each other. Similarly, with the exception of the projection 38, the inner side 36 of the bearing block 30 is substantially flat or slightly convex. A slightly convex inner side 36 is preferable for the same reason as discussed above.

Figure 7:
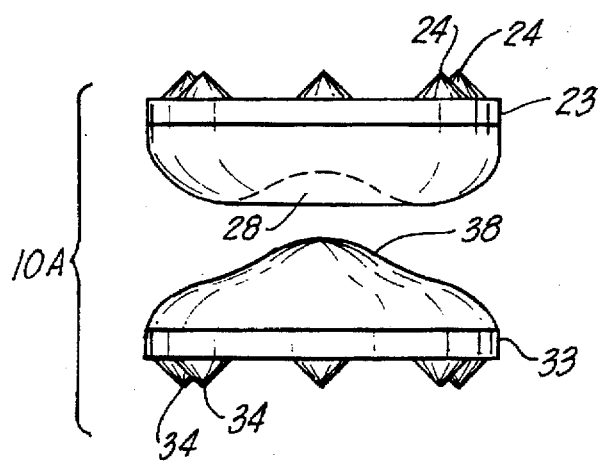
FIG. 7 is a side elevational exploded view of an alternate configuration of the present invention.

The artificial spinal disc 10 of the present invention is shaped so as to provide minimal restriction to bending and no restriction to rotational motion between the adjacent vertebrae, all of which are limitations found in other previous disc designs. In a preferred embodiment of the present invention, as shown in FIGS. 5 and 7, the edges of the recessed receiving mount 28 or socket segment recede quickly in order to maximize bending clearance. The edges of the recessed receiving mount 28 blend into the inner side 26 gradually and at a convex radius similar to that of the projection 38 in order to minimize contact stress and wear in extreme motion conditions. This feature also improves stability of the implant under extreme motion conditions. The projection 38 or ball segment likewise recedes quickly from the bearing region and blends gradually into the inner side 36. The projection 38 is preferably located approximately in the center of the implant 10 but may be designed such that the surgeon has an option of this location depending on patient needs.

The projection 38 of the bearing block 30 is of a generally hemispherical construction and conforms in shape to the concave surface of the receiving mount 28 such that the projection 38 is capable of rotating freely 360° in the recessed receiving mount 28. The shape of the recessed receiving mount 28 is substantially similar in curvature to the projection 38. The convex surface of projection 38 is of a depth or thickness that corresponds to or is greater than a depth of the concavity of the recessed receiving mount 28. In order to allow the supporting block 20 and the bearing block 30 to rotate freely in relation to each other, the depth or thickness of the convex surface of the projection 38 should be slightly greater than the depth of the concavity of the recessed receiving mount 28 assuming that the recessed receiving mount 28 and projection 38 are provided respectively with a flat surface.

Figure 6:
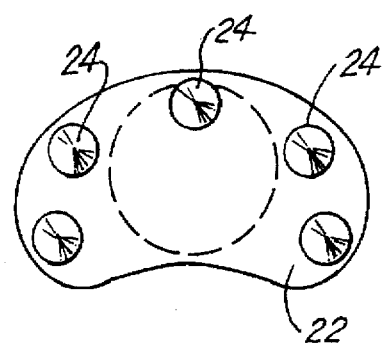
FIG. 6 is a end plan view of a first component of the present invention as shown in FIG. 5.
Figure 8:
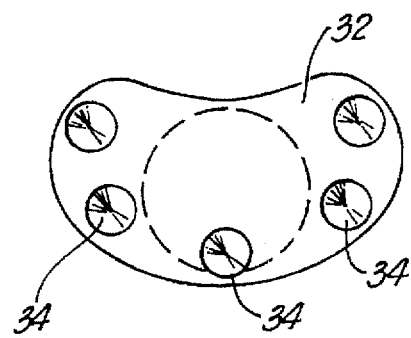
FIG. 8 is an end plan view of a second component of the present invention as shown in FIG. 5.

The intervertebral supporting block 20 and the intervertebral bearing block 30 have a total height or thickness that is dependent on the height or thickness of the deformed intervertebral disc that it is replacing. In addition, the supporting block 20 and the bearing block 30 have a shape that is dependent on the shape of the vertebrae adjacent to the intervertebral disc being replaced. In a preferred embodiment, the shape of the artificial spinal disc 10 is generally oval as shown in FIGS. 6 and 8.

The recessed receiving mount 28 of the artificial spinal disc 10 is located at or near the center of the supporting block 20. Likewise, the projection 38 of the artificial spinal disc 10 is located similarly at or near the center of the intervertebral bearing block 30.

The supporting block 20 and the bearing block 30 are provided respectively with one or more protuberances 24, 34 which can be in the form of pegs, posts or screws, and are located at any preselected position on the outer surfaces 22, 32 respectively of the supporting block 20 and bearing block 30. Additionally, flat beaded surfaces on the outer surfaces 22, 32 or other securing means can be used to hold the artificial spinal disc 10 in place in the adjacent vertebrae.

Figure 9:
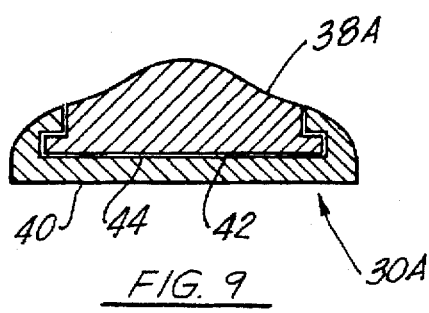
FIG. 9 is a side sectional view of an alternate embodiment of the present invention.

Translation of the primary wear surfaces is not necessary. However, in an alternate embodiment of spinal implant 10A, as shown in FIG. 9, a bearing block 30A has a projection or ball segment 38A and a base plate 40, similar in concept to a miniscal bearing knee, which allows for a certain mount of translation in combination with the rotation and bending allowed by the ball-socket design features. Alternatively, the supporting block 20, instead of the bearing block 30A, could have a recessed receiving mount and a base plate (not shown) identical to the bearing block 30A. This feature can improve the stability and resistance to dislocation of the implant 10A. In this alternate embodiment, a ceramic surface on a ceramic surface (in addition to metal—metal) can be employed for the two opposing, flat translating surfaces 42 44, as the contact stresses will be greatly reduced with such conformal surfaces. To avoid or minimize potential dislocation of the ball and socket, the base plates 40, 42, which can be formed of titanium or titanium alloy, can be attached to the supporting block 20A and the bearing block 30A mechanically or via shrink-fit or welding methods.

The intervertebral supporting block 20 and the intervertebral bearing block 30 can be made of metal material such stainless steel 316 LVM, or titanium-6-4, or cobalt/chrome alloy, which are all suitable for orthopedic surgery. In addition, a ceramic material such as hydroxyapatite, and the biologically compatible organic polymer such as HDPE may be used to make the artificial spinal disc 10 of the present invention.

In a preferred embodiment, the recessed receiving mount 28 and the projection 38 of the artificial spinal disc 10 are formed of a hard Cr-containing metal which is attached to titanium, titanium alloy, cobalt/chrome alloy, zirconium or zirconium alloy base components 23, 33 respectively as shown in FIG. 7. The preferred material for the base components 23, 33 is titanium or titanium alloy to minimize shadow effects from MRI imaging. Further, although bone cement may be used, the preferred embodiment utilizes a macro-textured or porous-coated outer side 22, 32 with the anchoring pegs or screws 24, 34 being porous-coated or macro-textured also.

The preferred material for the recessed receiving mount 28 and projection 38 is a Cr-containing iron or cobalt alloy with chromium in excess of about 15 weight % chromium, and the addition of about 2-6 weight % molybdenum to improve corrosion resistance in chloride-containing environments. Acceptable examples include A.I.S.I. 316 L stainless steel or ASTM F-75 cast Co—Cr—Mo or ASTM F-799 wrought Co—Cr—Mo alloy, all currently used in medical implant applications. However, due to the relatively high contact pressures incurred in ball-socket connections within the confined space between adjoining vertebrae, it is preferable to use a surface-hardened Cr-containing metal such as that described by Davidson in U.S. Pat. No. 5,415,704. Such alloy compositions produce minimal wear, are tolerant of three-body abrasion, and produce a relatively lubricious Cr/oxyhyroxide surface layer which enhances motion and wear resistance.

The present invention thus provides an unrestricted ball and socket-type artificial spinal disc containing low wear bearing surfaces of chromium containing metals, precision machined to minimize contact stress and anchored to the adjacent vertebrae with press fit or cemented methods known in the art of joint replacement. The artificial spinal disc 10 and 10A can be implanted to replace a degenerated or diseased intervertebral disc by conventional orthopedic surgery which is well known in the art.

The artificial spinal disc 10 and 10A is configured so as to allow the implant 10, 10A, to be implanted as a one piece unit rather than inserting one component at a time, which eliminates the need for over distraction of the adjacent vertebrae. In a bone resection technique that allows for the implantation of the implant as a single unit, openings or channels are formed in the bone of the adjacent vertebrae in a shape that conforms to the projections 24, 34. The implant 10, 10A is slid in place between the resection lines, as one unit, which prevents the need for over distraction, which can place unnecessary stresses on the surrounding structures.

Although the present invention has been described with reference to its preferred embodiments, those skilled in the art will recognize changes which may be made in form and structure which do not depart from the spirit of the invention already described in the specification and embodied in the claims which follow.

What is claimed is:

1. An artificial spinal disc for surgical placement between first and second adjacent vertebrae of a patient's spine, comprising:
   (a) a first component for attaching to the first vertebrae, said first component including a concave recess, the concave recess having a contoured surface with a circumference of 360°;
   (b) a second component for attaching to the second vertebrae, said second component including a projection that fits the concave recess of the first component, said projection having a convex contoured surface with a circumference of 360°;
   (c) the corresponding contoured surfaces being configured so as to allow an unrestricted rotational and a flexion/extension bending motion between the first and second components relative to a patient's normal spinal axis when in a standing position with the spine in a straightened position, said corresponding contoured surfaces allowing for a flexion/extension angle of about between 20° to 30°.

2. The artificial spinal disc of claim 1, wherein the contoured surface of at least one component is formed from a chromium-containing metal having a chromium content in excess of about 15 weight percent.

3. The artificial spinal disc of claim 1, wherein at least one contoured surface is formed from a cobalt-chromium-molybdenum alloy.

4. The artificial spinal disc of claim 1, wherein both contoured surfaces are formed from a cobalt-chromium-molybdenum alloy.

5. The artificial spinal disc of claim 1, wherein the first and second component include anchoring means for attachment to the respective first and second vertebrae.

6. The artificial spinal disc of claim 5, wherein the anchoring means is selected from the group consisting of pegs, posts and screws.

7. The artificial spinal disc of claim 5, wherein the anchoring means includes a surface selected from the group consisting of a porous-coated and a macro-textured surface to facilitate bone ingrowth.

8. An artificial spinal disc of claim 1, wherein the components are generally oval in shape with the contoured surfaces being positioned approximately in the center of the component.

9. An artificial spinal disc of claim 1, wherein the first and second components are configured so as to allow the artificial spinal disc to be implanted as one unit in which over distraction is eliminated.

10. An artificial spinal disc for surgical placement between first and second adjacent vertebrae of a patient's spine, comprising:
   (a) a first component for attaching to the first vertebrae, said first component including a concave recess, the concave recess having a contoured surface with a circumference of 360°;
   (b) a second component for attaching to the second vertebrae, said second component including a projection that fits the concave recess of the first component, said projection having a convex contoured surface with a circumference of 360°;
   (c) the corresponding contoured surfaces being configured so as to allow an unrestricted rotational and a flexion/extension bending motion between the first and second components relative to a patient's normal spinal axis when in a standing position with the spine in a straightened position, said corresponding contoured surfaces allowing for a flexion/extension angle of about between 20° to 30°;
   (d) wherein the first and second components are configured so as to allow the artificial spinal disc to be implanted as one unit in which openings in bone of the adjacent vertebrae are created in order to allow the artificial spinal disc to be slid into place so as to prevent over distraction.

* * * * *